US007922061B2

(12) United States Patent
Shelton, IV et al.

(10) Patent No.: US 7,922,061 B2
(45) Date of Patent: Apr. 12, 2011

(54) SURGICAL INSTRUMENT WITH AUTOMATICALLY RECONFIGURABLE ARTICULATING END EFFECTOR

(75) Inventors: Frederick E. Shelton, IV, Hillsboro, OH (US); David C. Yates, West Chester, OH (US); Richard C. Smith, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 101 days.

(21) Appl. No.: 12/124,655

(22) Filed: May 21, 2008

(65) Prior Publication Data
US 2009/0289096 A1  Nov. 26, 2009

(51) Int. Cl.
*A61B 17/32* (2006.01)
(52) U.S. Cl. .............. 227/175.1; 227/176.1; 227/180.1
(58) Field of Classification Search ............... 227/175.1, 227/176.1, 180.1
See application file for complete search history.

(56) References Cited

U.S. PATENT DOCUMENTS

| 4,429,695 A | 2/1984 | Green |
| 4,809,695 A | 3/1989 | Gwathmey et al. |
| 5,188,111 A | 2/1993 | Yates et al. |
| 5,413,272 A | 5/1995 | Green et al. |
| 5,417,361 A | 5/1995 | Williamson, IV |
| 5,480,089 A | 1/1996 | Blewett |
| 5,485,947 A | 1/1996 | Olson et al. |
| 5,487,499 A | 1/1996 | Sorrentino et al. |
| 5,489,058 A | 2/1996 | Plyley et al. |
| 5,497,933 A | 3/1996 | DeFonzo et al. |
| 5,503,320 A | 4/1996 | Webster et al. |
| 5,509,596 A | 4/1996 | Green et al. |
| 5,529,235 A | 6/1996 | Boiarski et al. |
| 5,535,934 A | 7/1996 | Boiarski et al. |
| 5,553,765 A | 9/1996 | Knodel et al. |
| 5,560,530 A | 10/1996 | Bolanos et al. |
| 5,560,532 A | 10/1996 | DeFonzo et al. |
| 5,562,241 A | 10/1996 | Knodel et al. |
| 5,564,615 A | 10/1996 | Bishop et al. |

(Continued)

FOREIGN PATENT DOCUMENTS

CA    2458946 A1    3/2003

(Continued)

OTHER PUBLICATIONS

International Search Report, PCT/US2009/044428, Sep. 10, 2009 (7 pages).

(Continued)

*Primary Examiner* — Paul R Durand
*Assistant Examiner* — Nathaniel Chukwurah (57) ABSTRACT

A surgical instrument, such as a surgical cutting and fastening instrument, with an automatically articulatable end effector. The surgical instrument may comprise an end effector, a shaft, and an articulatable joint assembly connected between the end effector and the shaft. The joint assembly comprises at least one motor for articulating the end effector relative to the shaft. The joint assembly comprises at least one articulation sensor for sensing articulation of the end effector relative to the shaft. The instrument further comprises a control unit in communication with the articulation sensor and the motor. The control unit comprises at least one memory unit for storing articulation data from the at least one articulation sensor. When activated, the control unit sends control signals to the motor of the joint assembly to articulate automatically the end effector to a desired position based on the articulation data from the articulation sensor that is stored in the memory unit of the control unit.

12 Claims, 5 Drawing Sheets

U.S. PATENT DOCUMENTS

| | | | |
|---|---|---|---|
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,605,273 A | 2/1997 | Hamblin et al. |
| 5,607,094 A | 3/1997 | Clark et al. |
| 5,626,595 A | 5/1997 | Sklar et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,634,584 A | 6/1997 | Okorocha et al. |
| 5,636,780 A | 6/1997 | Green et al. |
| 5,639,008 A | 6/1997 | Gallagher et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,688,270 A | 11/1997 | Yates et al. |
| 5,690,269 A | 11/1997 | Bolanos et al. |
| 5,692,668 A | 12/1997 | Schulze et al. |
| 5,697,543 A | 12/1997 | Burdorff |
| 5,704,534 A | 1/1998 | Huitema et al. |
| 5,709,680 A | 1/1998 | Yates et al. |
| 5,711,472 A | 1/1998 | Bryan |
| 5,715,987 A | 2/1998 | Kelley et al. |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,820,009 A | 10/1998 | Melling et al. |
| 5,826,776 A | 10/1998 | Schulze et al. |
| 5,836,503 A | 11/1998 | Ehrenfels et al. |
| 5,839,639 A | 11/1998 | Sauer et al. |
| 5,851,179 A * | 12/1998 | Ritson et al. ............... 600/338 |
| 5,855,311 A | 1/1999 | Hamblin et al. |
| 5,865,361 A | 2/1999 | Milliman et al. |
| 5,901,895 A | 5/1999 | Heaton et al. |
| 5,911,353 A | 6/1999 | Bolanos et al. |
| 5,941,442 A | 8/1999 | Geiste et al. |
| 5,954,259 A | 9/1999 | Viola et al. |
| 6,010,054 A | 1/2000 | Johnson et al. |
| 6,032,849 A | 3/2000 | Mastri et al. |
| 6,102,271 A | 8/2000 | Longo et al. |
| 6,119,913 A | 9/2000 | Adams et al. |
| 6,126,058 A | 10/2000 | Adams et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,330,965 B1 | 12/2001 | Milliman et al. |
| 6,488,197 B1 | 12/2002 | Whitman |
| 6,491,201 B1 | 12/2002 | Whitman |
| 6,505,768 B2 | 1/2003 | Whitman |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,619,529 B2 | 9/2003 | Green et al. |
| 6,644,532 B2 | 11/2003 | Green et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,769,594 B2 | 8/2004 | Orban, III |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,309 B2 | 1/2005 | Whitman et al. |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,070,083 B2 | 7/2006 | Jankowski |
| 7,080,769 B2 | 7/2006 | Vresh et al. |
| 7,083,075 B2 | 8/2006 | Swayze et al. |
| 7,114,642 B2 | 10/2006 | Whitman |
| 7,121,446 B2 | 10/2006 | Arad et al. |
| 7,128,253 B2 | 10/2006 | Mastri et al. |
| 7,140,527 B2 | 11/2006 | Ehrenfels et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,188,758 B2 | 3/2007 | Viola et al. |
| 7,210,609 B2 | 5/2007 | Leiboff et al. |
| 7,213,736 B2 | 5/2007 | Wales et al. |
| 7,225,964 B2 | 6/2007 | Mastri et al. |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,438,209 B1 | 10/2008 | Hess et al. |

| | | |
|---|---|---|
| 7,441,685 B1 | 10/2008 | Boudreaux |
| 7,481,347 B2 | 1/2009 | Roy |
| 7,490,749 B2 | 2/2009 | Schall et al. |
| 7,494,039 B2 | 2/2009 | Racenet et al. |
| 7,506,790 B2 | 3/2009 | Shelton, IV |
| 7,510,107 B2 | 3/2009 | Timm et al. |
| 7,546,940 B2 | 6/2009 | Milliman et al. |
| 7,549,564 B2 | 6/2009 | Boudreaux |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,631,793 B2 | 12/2009 | Rethy et al. |
| 7,658,311 B2 | 2/2010 | Boudreaux |
| 7,665,646 B2 | 2/2010 | Prommersberger |
| 2002/0117534 A1 | 8/2002 | Green et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2005/0103819 A1 | 5/2005 | Racenet et al. |
| 2005/0184121 A1 | 8/2005 | Heinrich |
| 2005/0189397 A1 | 9/2005 | Jankowski |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0025811 A1 | 2/2006 | Shelton, IV |
| 2006/0025812 A1 | 2/2006 | Shelton, IV |
| 2006/0049229 A1 | 3/2006 | Milliman et al. |
| 2006/0180634 A1 | 8/2006 | Shelton, IV et al. |
| 2006/0212069 A1 | 9/2006 | Shelton, IV |
| 2006/0226196 A1 | 10/2006 | Hueil et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1* | 2/2007 | Whitman et al. ......... 227/175.1 |
| 2007/0045379 A1 | 3/2007 | Shelton, IV |
| 2007/0073340 A1 | 3/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1* | 5/2007 | Shelton et al. ................ 606/170 |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0246505 A1 | 10/2007 | Pace-Floridia et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314955 A1 | 12/2008 | Boudreaux et al. |
| 2008/0314957 A1 | 12/2008 | Boudreaux |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |

| | | | | | | |
|---|---|---|---|---|---|---|
| 2009/0206138 | A1 | 8/2009 | Smith et al. | EP | 0603472 B1 | 11/1998 |
| 2009/0206139 | A1 | 8/2009 | Hall et al. | EP | 0605351 B1 | 11/1998 |
| 2009/0206140 | A1 | 8/2009 | Scheib et al. | EP | 0878169 A1 | 11/1998 |
| 2009/0206141 | A1 | 8/2009 | Huitema et al. | EP | 0879742 A1 | 11/1998 |
| 2009/0206142 | A1 | 8/2009 | Huitema et al. | EP | 0760230 B1 | 2/1999 |
| 2009/0206143 | A1 | 8/2009 | Huitema et al. | EP | 0537572 B1 | 6/1999 |
| 2009/0206144 | A1 | 8/2009 | Doll et al. | EP | 0552050 B1 | 5/2000 |
| 2009/0209946 | A1 | 8/2009 | Swayze et al. | EP | 1090592 A1 | 4/2001 |
| 2009/0218384 | A1 | 9/2009 | Aranyi | EP | 1256318 B1 | 5/2001 |
| 2009/0242610 | A1 | 10/2009 | Shelton, IV et al. | EP | 0908152 B1 | 1/2002 |
| 2009/0255974 | A1 | 10/2009 | Viola | EP | 0872213 B1 | 5/2002 |
| 2009/0255978 | A1 | 10/2009 | Viola et al. | EP | 1238634 A2 | 9/2002 |
| 2010/0032470 | A1 | 2/2010 | Hess et al. | EP | 0656188 B1 | 1/2003 |
| 2010/0065605 | A1 | 3/2010 | Shelton, IV et al. | EP | 0829235 B1 | 6/2003 |
| 2010/0065609 | A1 | 3/2010 | Schwemberger | EP | 0813843 B1 | 10/2003 |
| 2010/0069942 | A1 | 3/2010 | Shelton, IV | EP | 0741996 B1 | 2/2004 |
| 2010/0072251 | A1 | 3/2010 | Baxter, III et al. | EP | 0705570 B1 | 4/2004 |
| 2010/0072252 | A1 | 3/2010 | Baxter, III et al. | EP | 1086713 B1 | 5/2004 |
| 2010/0072253 | A1 | 3/2010 | Baxter, III et al. | EP | 1426012 A1 | 6/2004 |
| 2010/0072256 | A1 | 3/2010 | Baxter, III et al. | EP | 0888749 B1 | 9/2004 |
| 2010/0076474 | A1 | 3/2010 | Yates et al. | EP | 1477119 A1 | 11/2004 |
| 2010/0076475 | A1 | 3/2010 | Yates et al. | EP | 1479345 A1 | 11/2004 |
| 2010/0089970 | A1 | 4/2010 | Smith et al. | EP | 1479347 A1 | 11/2004 |
| 2010/0089974 | A1 | 4/2010 | Shelton, IV | EP | 1479348 A1 | 11/2004 |
| 2010/0096435 | A1 | 4/2010 | Fuchs et al. | EP | 1520521 A1 | 4/2005 |
| 2010/0133317 | A1 | 6/2010 | Shelton, IV et al. | EP | 1520523 A1 | 4/2005 |
| 2010/0133318 | A1 | 6/2010 | Boudreaux | EP | 1520525 A1 | 4/2005 |
| 2010/0179382 | A1 | 7/2010 | Shelton, IV et al. | EP | 1522264 A1 | 4/2005 |
| 2010/0181364 | A1 | 7/2010 | Shelton, IV et al. | EP | 1550408 A1 | 7/2005 |
| 2010/0193566 | A1 | 8/2010 | Scheib et al. | EP | 1557129 A1 | 7/2005 |
| 2010/0193567 | A1 | 8/2010 | Scheib et al. | EP | 1064883 B1 | 8/2005 |
| 2010/0193568 | A1 | 8/2010 | Scheib et al. | EP | 1157666 B1 | 9/2005 |
| 2010/0193569 | A1 | 8/2010 | Yates et al. | EP | 1621138 A2 | 2/2006 |
| 2010/0198220 | A1 | 8/2010 | Boudreaux et al. | EP | 1621139 A2 | 2/2006 |
| 2010/0213241 | A1 | 8/2010 | Bedi et al. | EP | 1621141 A2 | 2/2006 |
| | | | | EP | 1621145 A2 | 2/2006 |
| | FOREIGN PATENT DOCUMENTS | | | EP | 1621151 A2 | 2/2006 |
| CA | 2512960 | A1 | 1/2006 | EP | 1652481 A2 | 5/2006 |
| CA | 2514274 | A1 | 1/2006 | EP | 1382303 B1 | 6/2006 |
| DE | 273689 | C | 5/1914 | EP | 1045672 B1 | 8/2006 |
| DE | 1775926 | A | 1/1972 | EP | 1617768 B1 | 8/2006 |
| DE | 9412228 | U | 9/1994 | EP | 1702567 A2 | 9/2006 |
| DE | 19924311 | A1 | 11/2000 | EP | 1129665 B1 | 11/2006 |
| DE | 69328576 | T2 | 1/2001 | EP | 1256317 B1 | 12/2006 |
| DE | 20112837 | U1 | 10/2001 | EP | 1728473 A1 | 12/2006 |
| DE | 20121753 | U1 | 4/2003 | EP | 1728475 A2 | 12/2006 |
| DE | 10314072 | A1 | 10/2004 | EP | 1479346 B1 | 1/2007 |
| EP | 0122046 | A1 | 10/1984 | EP | 1484024 B1 | 1/2007 |
| EP | 0070230 | B1 | 10/1985 | EP | 1754445 A2 | 2/2007 |
| EP | 0033548 | B1 | 5/1986 | EP | 1759812 A1 | 3/2007 |
| EP | 0276104 | A2 | 7/1988 | EP | 1769756 A1 | 4/2007 |
| EP | 0639349 | A2 | 2/1994 | EP | 1769758 A1 | 4/2007 |
| EP | 0324636 | B1 | 3/1994 | EP | 1785097 A1 | 5/2007 |
| EP | 0593920 | A1 | 4/1994 | EP | 1790293 A2 | 5/2007 |
| EP | 0600182 | A2 | 6/1994 | EP | 1800610 A1 | 6/2007 |
| EP | 0630612 | A1 | 12/1994 | EP | 1300117 B1 | 8/2007 |
| EP | 0634144 | A1 | 1/1995 | EP | 1813199 A1 | 8/2007 |
| EP | 0646356 | A2 | 4/1995 | EP | 1813201 A1 | 8/2007 |
| EP | 0646357 | A1 | 4/1995 | EP | 1813203 A2 | 8/2007 |
| EP | 0653189 | A2 | 5/1995 | EP | 1813207 A1 | 8/2007 |
| EP | 0669104 | A1 | 8/1995 | EP | 1813209 A1 | 8/2007 |
| EP | 0511470 | B1 | 10/1995 | EP | 1839596 A1 | 10/2007 |
| EP | 0679367 | A2 | 11/1995 | EP | 1402821 B1 | 12/2007 |
| EP | 0392547 | B1 | 12/1995 | EP | 1872727 A1 | 1/2008 |
| EP | 0685204 | A1 | 12/1995 | EP | 1897502 A1 | 3/2008 |
| EP | 0699418 | A1 | 3/1996 | EP | 1702568 B1 | 7/2008 |
| EP | 0702937 | A1 | 3/1996 | EP | 1970014 A1 | 9/2008 |
| EP | 0705571 | A1 | 4/1996 | EP | 1980213 A2 | 10/2008 |
| EP | 0484677 | B2 | 6/1996 | EP | 1759645 B1 | 11/2008 |
| EP | 0541987 | B1 | 7/1996 | EP | 1693008 B1 | 12/2008 |
| EP | 0667119 | B1 | 7/1996 | EP | 2000102 A2 | 12/2008 |
| EP | 0770355 | A1 | 5/1997 | EP | 1749486 B1 | 3/2009 |
| EP | 0503662 | B1 | 6/1997 | EP | 2090256 A2 | 8/2009 |
| EP | 0578425 | B1 | 9/1997 | EP | 1813206 B1 | 4/2010 |
| EP | 0625335 | B1 | 11/1997 | FR | 999646 | A | 2/1952 |
| EP | 0552423 | B1 | 1/1998 | FR | 1112936 | A | 3/1956 |
| EP | 0592244 | B1 | 1/1998 | FR | 2765794 | A | 1/1999 |
| EP | 0648476 | B1 | 1/1998 | GB | 939929 | A | 10/1963 |
| EP | 0676173 | B1 | 9/1998 | GB | 1210522 | A | 10/1970 |

| | | | |
|---|---|---|---|
| GB | 2336214 A | 10/1999 | |
| JP | 6007357 A | 1/1994 | |
| JP | 7051273 A | 2/1995 | |
| JP | 8033641 A | 2/1996 | |
| JP | 8229050 A | 9/1996 | |
| JP | 2000287987 A | 10/2000 | |
| JP | 2001286477 A | 10/2001 | |
| JP | 2002369820 A | 12/2002 | |
| JP | 2005505322 T | 2/2005 | |
| JP | 2005103293 A | 4/2005 | |
| RU | 2187249 C2 | 8/2002 | |
| RU | 2225170 C2 | 3/2004 | |
| SU | 1377053 A1 | 2/1988 | |
| SU | 1561964 A1 | 5/1990 | |
| SU | 1722476 A1 | 3/1992 | |
| WO | WO 93/08755 A1 | 5/1993 | |
| WO | WO 95/18572 A1 | 7/1995 | |
| WO | WO 95/23557 A1 | 9/1995 | |
| WO | WO 95/29639 A1 | 11/1995 | |
| WO | WO 96/22055 A1 | 7/1996 | |
| WO | WO 96/35464 A1 | 11/1996 | |
| WO | WO 97/34533 A1 | 9/1997 | |
| WO | WO 97/39688 A2 | 10/1997 | |
| WO | WO 98/17180 A1 | 4/1998 | |
| WO | WO 98/30153 A1 | 7/1998 | |
| WO | WO 99/12483 A1 | 3/1999 | |
| WO | WO 99/15086 A1 | 4/1999 | |
| WO | WO 99/34744 A1 | 7/1999 | |
| WO | WO 99/45849 A1 | 9/1999 | |
| WO | WO 00/24322 A1 | 5/2000 | |
| WO | WO 00/57796 A1 | 10/2000 | |
| WO | WO 00/64365 A1 | 11/2000 | |
| WO | WO 00/72762 A1 | 12/2000 | |
| WO | WO 00/72765 A1 | 12/2000 | |
| WO | WO 01/05702 A1 | 1/2001 | |
| WO | WO 01/10482 A1 | 2/2001 | |
| WO | WO 01/54594 A1 | 8/2001 | |
| WO | WO 01/62158 A2 | 8/2001 | |
| WO | WO 01/62162 A1 | 8/2001 | |
| WO | WO 01/62164 A2 | 8/2001 | |
| WO | WO 01/91646 A1 | 12/2001 | |
| WO | WO 02/07608 A2 | 1/2002 | |
| WO | WO 02/07618 A1 | 1/2002 | |
| WO | WO 02/17799 A1 | 3/2002 | |
| WO | WO 02/19920 A1 | 3/2002 | |
| WO | WO 02/30297 A2 | 4/2002 | |
| WO | WO 02/32322 A2 | 4/2002 | |
| WO | WO 02/43571 A2 | 6/2002 | |
| WO | WO 02/058568 A1 | 8/2002 | |
| WO | WO 02/060328 A1 | 8/2002 | |
| WO | WO 02/067785 A2 | 9/2002 | |
| WO | WO 02/098302 A1 | 12/2002 | |
| WO | WO 03/000138 A2 | 1/2003 | |
| WO | WO 03/001329 A2 | 1/2003 | |
| WO | WO 03/013363 A1 | 2/2003 | |
| WO | WO 03/020106 A2 | 3/2003 | |
| WO | WO 03/020139 A2 | 3/2003 | |
| WO | WO 03/079909 A3 | 3/2003 | |
| WO | WO 03/030743 A2 | 4/2003 | |
| WO | WO 03/037193 A1 | 5/2003 | |
| WO | WO 03/047436 A3 | 6/2003 | |
| WO | WO 03/057048 A1 | 7/2003 | |
| WO | WO 03/057058 A1 | 7/2003 | |
| WO | WO 03/063694 A1 | 8/2003 | |
| WO | WO 03/077769 A1 | 9/2003 | |
| WO | WO 03/082126 A1 | 10/2003 | |
| WO | WO 03/088845 A2 | 10/2003 | |
| WO | WO 03/090630 A2 | 11/2003 | |
| WO | WO 03/094743 A1 | 11/2003 | |
| WO | WO 03/094745 A1 | 11/2003 | |
| WO | WO 03/094746 A1 | 11/2003 | |
| WO | WO 03/094747 A1 | 11/2003 | |
| WO | WO 03/101313 A1 | 12/2003 | |
| WO | WO 03/105698 A2 | 12/2003 | |
| WO | WO 03/105702 A2 | 12/2003 | |
| WO | WO 2004/006980 A2 | 1/2004 | |
| WO | WO 2004/028585 A2 | 4/2004 | |
| WO | WO 2004/032754 A2 | 4/2004 | |
| WO | WO 2004/032760 A2 | 4/2004 | |
| WO | WO 2004/032762 A1 | 4/2004 | |
| WO | WO 2004/032763 A2 | 4/2004 | |
| WO | WO 2004/047653 A2 | 6/2004 | |
| WO | WO 2004/049956 A2 | 6/2004 | |
| WO | WO 2004/086987 A1 | 10/2004 | |
| WO | WO 2004/096057 A2 | 11/2004 | |
| WO | WO 2004/105621 A1 | 12/2004 | |
| WO | WO 2004/112618 A2 | 12/2004 | |
| WO | WO 2004/112652 A2 | 12/2004 | |
| WO | WO 2005/027983 A2 | 3/2005 | |
| WO | WO 2005/037329 A2 | 4/2005 | |
| WO | WO 2005/078892 A1 | 8/2005 | |
| WO | WO 2005/096954 A2 | 10/2005 | |
| WO | WO 2005/112808 A1 | 12/2005 | |
| WO | WO 2005/115251 A2 | 12/2005 | |
| WO | WO 2006/044490 A2 | 4/2006 | |
| WO | WO 2006/044581 A2 | 4/2006 | |
| WO | WO 2006/044810 A2 | 4/2006 | |
| WO | WO 2006/083748 A1 | 8/2006 | |
| WO | WO 2006/115958 A1 | 11/2006 | |
| WO | WO 2006/132992 A1 | 12/2006 | |
| WO | WO 2007/002180 A2 | 1/2007 | |
| WO | WO 2007/016290 A2 | 2/2007 | |
| WO | WO 2007/018898 A2 | 2/2007 | |
| WO | WO 2007/098220 A2 | 8/2007 | |
| WO | WO 2007/121579 A1 | 11/2007 | |
| WO | WO 2007/137304 A2 | 11/2007 | |
| WO | WO 2007/139734 A2 | 12/2007 | |
| WO | WO 2007/142625 A2 | 12/2007 | |
| WO | WO 2008/039270 A1 | 4/2008 | |
| WO | WO 2008/045383 A2 | 4/2008 | |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

U.S. Appl. No. 12/032,024, filed Feb. 15, 2008.

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

* cited by examiner

SURGICAL INSTRUMENT WITH AUTOMATICALLY RECONFIGURABLE ARTICULATING END EFFECTOR

BACKGROUND

Surgical staplers have been used in the prior art to simultaneously make a longitudinal incision in tissue and apply lines of staples on opposing sides of the incision. Such instruments commonly include an end effector having a pair of cooperating jaw members that, if the instrument is intended for endoscopic or laparoscopic applications, are capable of passing through a cannula passageway. One of the jaw members receives a staple cartridge having at least two laterally spaced rows of staples—one on each side of the knife channel. The other jaw member defines an anvil having staple-forming pockets aligned with the rows of staples in the cartridge. The instrument includes a plurality of reciprocating wedges that, when driven distally, pass through openings in the staple cartridge and engage drivers supporting the staples to effect the firing of the staples toward the anvil. Simultaneously, a cutting instrument (or knife) that is drawn distally along the jaw member so that the clamped tissue is cut and fastened (e.g., stapled) at the same time.

An example of a surgical stapler suitable for endoscopic applications is described in U.S. Pat. No. 7,000,818 B2, entitled, "Surgical stapling instrument having separate distinct closing and firing systems," the disclosure of which is herein incorporated by reference in its entirety. In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling actions avoid complications that may arise when performing such actions sequentially with different surgical tools that respectively only sever or staple.

The prior art also includes endocutters with articulatable end effectors, such as described in published U.S. patent application Pub. No. 2007/0175959, which is incorporated herein by reference in its entirety. Such an instrument comprises an articulation control that allows a user (e.g., an operating surgeon) to effect rotation of the end effector about an articulation pivot.

Commonly, a procedure that requires use of such an endocutter requires the operator to undertake several cutting/fastening strokes at a general common location within the patient. Thus, after each cutting/fastening stroke by the instrument, the clinician has to withdraw the instrument through the cannula and replace the now-spent staple cartridge in the end effector. Then the clinician has to reinsert the instrument back through the cannula into the patient and position the end effector again, including articulating the end effector back to the same general position it was in for the prior cutting/fastening stroke.

SUMMARY

In one general aspect, the present invention is directed to a surgical instrument, such as a surgical cutting and fastening instrument, with an automatically articulatable end effector. According to various embodiments, the surgical instrument may comprise an end effector, a shaft, and an articulatable joint assembly connected between the end effector and the shaft. The joint assembly comprises at least one motor for articulating the end effector relative to the shaft. The joint assembly also comprises at least one articulation sensor for sensing articulation of the end effector relative to the shaft.

The instrument further comprises a control unit in communication with the articulation sensor and the motor. The control unit comprises at least one memory unit for storing articulation data from the at least one articulation sensor. In addition, when activated, the control unit sends control signals to the motor of the joint assembly to articulate automatically the end effector to a desired position (or articulation state) based on the articulation data from the articulation sensor that is stored in the memory unit of the control unit. For example, the control unit may cause the end effector to articulate to a prior state of articulation (such as the state of articulation when the instrument was last fired) or some other state of articulation. The control unit may also be able to cause the end effector to automatically articulate back to its original or unarticulated state. That way, a clinician can (i) insert the end effector into a patient through a cannula, (ii) automatically articulate the end effector to a desired position, (iii) fire the instrument, (iv) rearticulate the end effector back to its original state to (v) withdraw it from the patient through the cannula, and (vi) replace the cartridge so that the process can be repeated. This should tend to lead to greater accuracy and repeatability in repositioning the end effector, which is important in procedures where the end effector needs to be position in the same general position for repeated firings.

According to various implementations, the surgical instrument may be a surgical cutting and fastening instrument, such as an endocutter. As such, the end effector may comprise two opposing, pivotably connected jaw members. One jaw member may carry a cutting instrument for severing tissue clamped between the two jaw members. It may also comprise a replaceable staple cartridge carrying a number of staples, such that when the instrument is fired, the staples are urged through the clamped tissue and turned by the other jaw member, acting as an anvil.

In another general aspect, the present invention is directed to a method of performing a surgical procedure. In one embodiment, the process comprises: (a) inserting the articulatable end effector into the patient through the cannula while the end effector is in a first articulation state; (b) after step (a), activating an input device on the surgical instrument to cause the end effector to automatically articulate to a second articulation state that is different from the first articulation state; (c) after step (b), firing the surgical instrument to sever and fasten tissue clamped in the end effector; (d) after step (c), activating the input device to cause the end effector to automatically articulate to the first articulation state; and (e) after step (d), withdrawing the end effector from the patient through the cannula.

These and other benefits of the present invention will be apparent from the description below.

FIGURES

Various embodiments of the present invention are described herein by way of example in conjunction with the following figures, wherein.

DESCRIPTION

Figure 1:
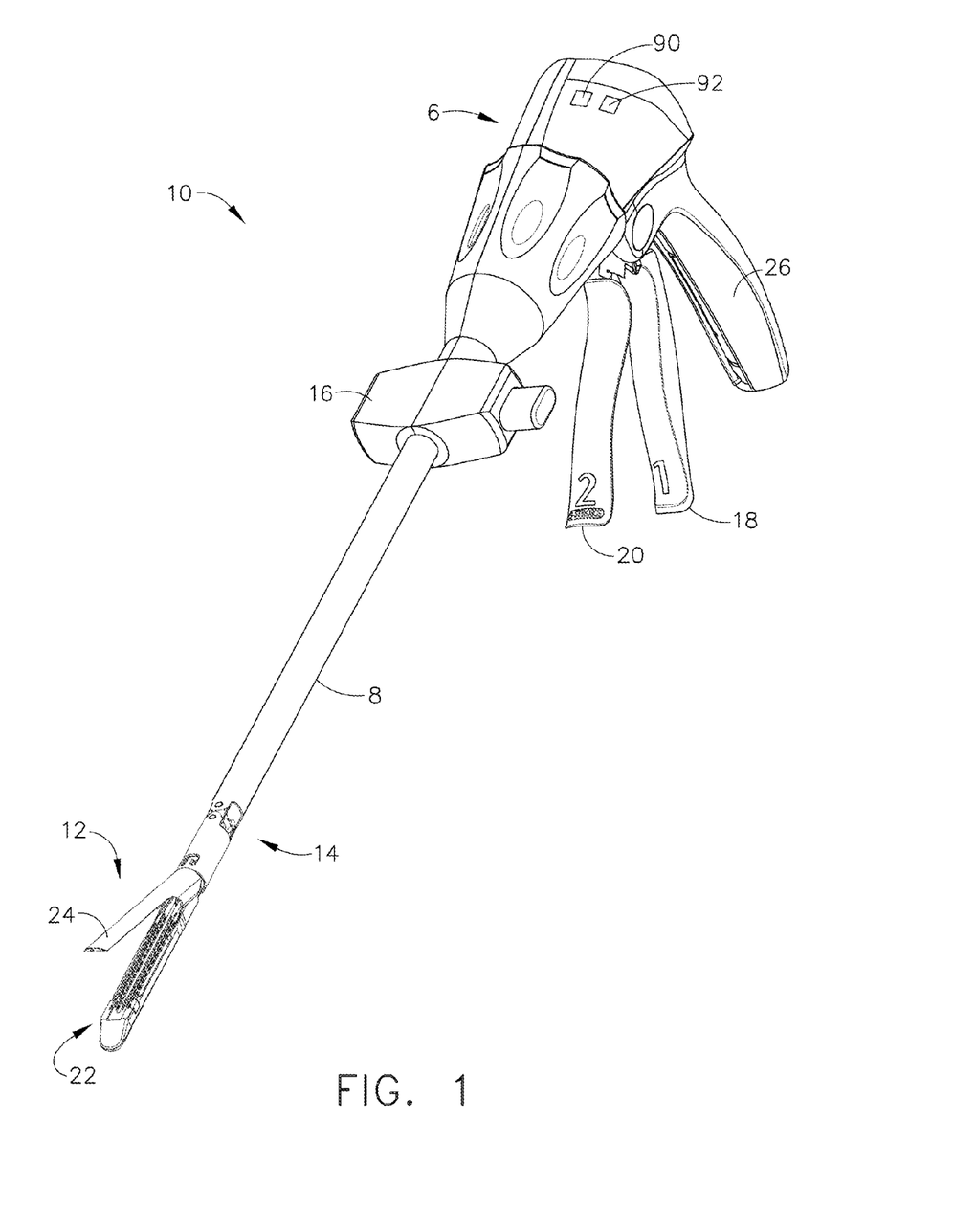
FIGS. 1 and 2 depict a surgical instrument with an articulatable end effector according to various embodiments of the present invention.
Figure 2:
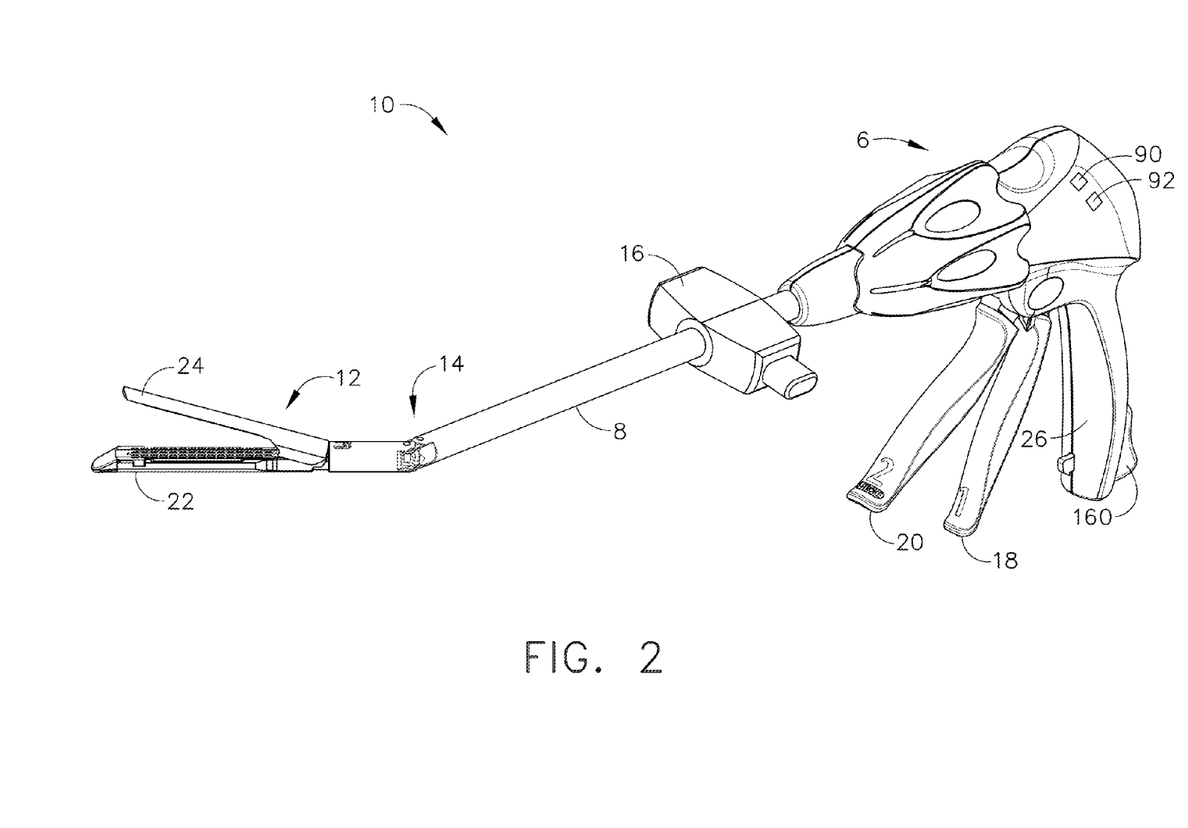

FIGS. 1 and 2 depict a surgical cutting and fastening instrument 10 with an automatically articulatable end effector according to various embodiments of the present invention. The illustrated embodiment is an endoscopic surgical instrument 10 and in general, the embodiments of the instrument 10 described herein are endoscopic surgical cutting and fastening instruments. It should be noted, however, that according to other embodiments of the present invention, the instrument 10 may be a non-endoscopic surgical cutting instrument, such as a laproscopic instrument, with an automatically articulatable end effector.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing, and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16. One type of suitable articulation control is described in published U.S. patent application Pub. No. 2007/0158385 A1, entitled "Surgical Instrument Having An Articulating End Effector," by Geoffrey C. Hueil et al., which is incorporated herein by reference in its entirety.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 toward which a closure trigger 18 is pivotally drawn by the clinician to cause clamping or closing of the anvil 24 towards the staple channel 22 of the end effector 12 to thereby clamp tissue positioned between the anvil 24 and channel 22. In the illustrated embodiment, the firing trigger 20 is farther outboard of the closure trigger 18. According to such an embodiment, once the closure trigger 18 is locked in the closure position, the firing trigger 20 may rotate slightly toward the pistol grip 26 so that it can be reached by the operator using one hand. Then the operator may pivotally draw the firing trigger 20 toward the pistol grip 26 to cause the stapling and severing of clamped tissue in the end effector 12. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

In use, the closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure. A release button on the handle 6, when depressed, may release the locked closure trigger 18.

As shown in FIGS. 1-2, the handle 6 may comprise one or multiple external user input selection devices 90, 92, which may be, for example, a push-button switch(es), a toggle switch(es), a dial(s), a membrane switch(es), a microphone, a touchscreen, a trackball, or any other suitable type of switch or user input device, that allows the operator of the instrument 10 to automatically articulate the end effector 12 to its prior state of articulation and back to its original/normal state (e.g., no articulation). More details regarding this feature are provided below.

Figure 3:
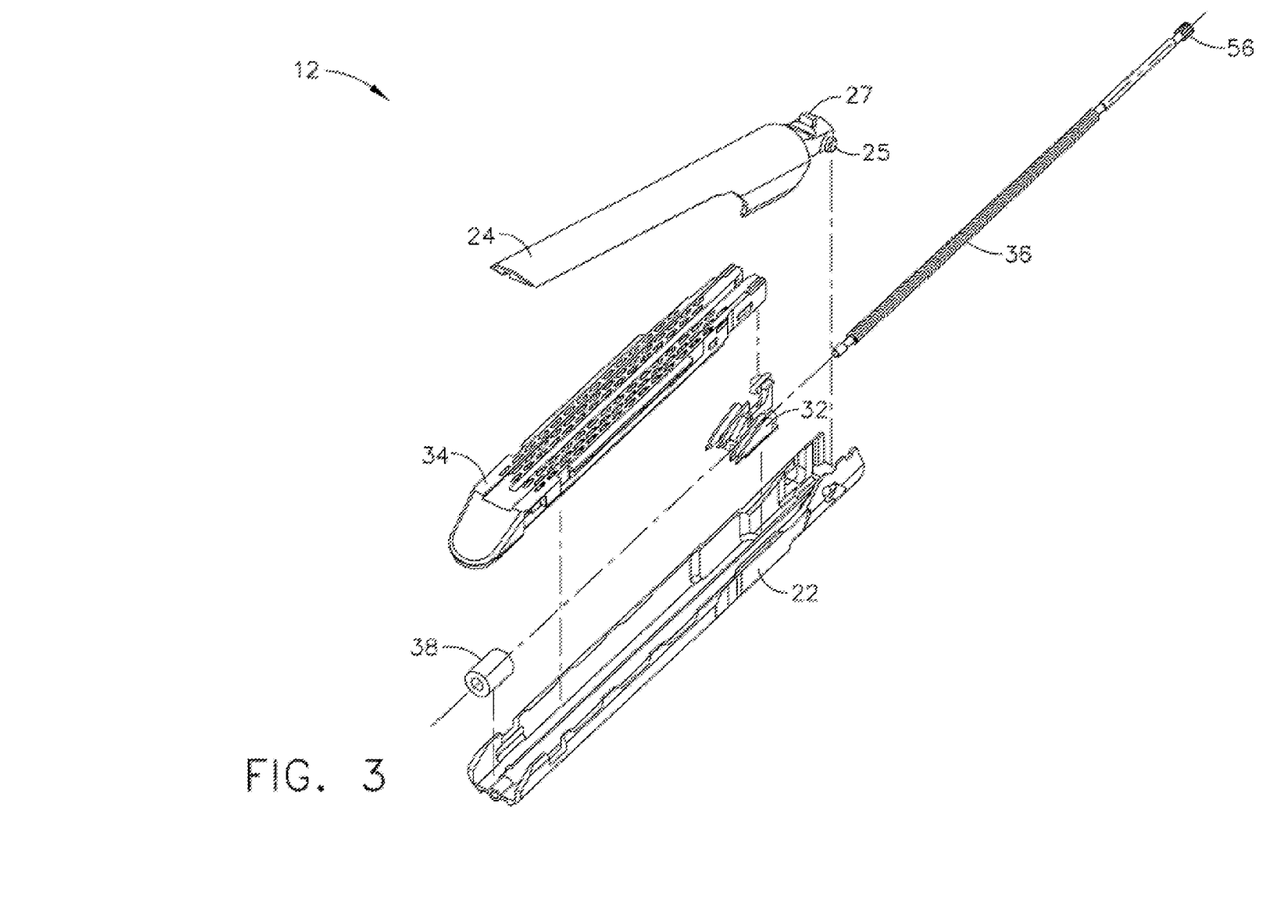
FIG. 3 is an exploded view of the end effector of the surgical instrument of FIGS. 1 and 2 according to various embodiments of the present invention.

FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of a mechanical closure system to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. In various embodiments, the sled 33 maybe an integral component of the cartridge 34. U.S. Pat. No. 6,978,921, entitled "Surgical stapling instrument incorporating an E-beam firing mechanism," which is incorporated herein by reference in its entirety, provides more details about such two-stroke cutting and fastening instruments The sled 33 may be part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled "ELECTROSURGICAL HEMOSTATIC DEVICE," to Yates et al., and U.S. Pat. No. 5,688,270 entitled "ELECTROSURGICAL HEMOSTATIC DEVICE WITH RECESSED AND/OR OFFSET ELECTRODES" to Yates et al., which are incorporated herein by reference in their entirety, disclose an endoscopic cutting instrument that uses RF energy to seal the severed tissue.

Published U.S. patent application Pub. No. 2007/0102453, entitled "Surgical stapling instruments structured for delivery of medical agents," to Jerome R. Morgan, et. al, and published U.S. patent application Pub. No. 2007/0102452, entitled "Surgical stapling instruments structured for pump-assisted delivery of medical agents," to Frederick E. Shelton, IV, et. al., which are incorporated herein by reference in their entirety also, disclose an endoscopic cutting instrument that uses adhesives to fasten the severed tissue. Accordingly, although the description herein generally refers to cutting/ stapling operations and the like, it should be recognized that this is an exemplary embodiment and is not meant to be limiting. Other tissue-fastening techniques may also be used.

More details regarding suitable end effectors, closure trigger locking mechanisms, and mechanical closure systems for the end effector may be found in published U.S. patent application Pub. No. 2007/0175958 A1, entitled "Motor-driven surgical cutting and fastening instrument with user feedback system," by Shelton et al., which is incorporated herein by reference in its entirety.

The instrument 10 may also comprise an electric motor for powering the end effector 12. Published U.S. patent application Pub. No. 2007/0175958 A1, referred to in the preceding paragraph, discloses an endocutter having an electric motor for powering the end effector. In such an embodiment, the motor, which may be powered by a battery (or batteries) in the handle, powers, through a drive train, the related cutting and fastening operations of the end effector.

The instrument 10 may also include a number of sensors that sense various conditions related to the instrument 10. For example, as described in published U.S. patent application Pub. No. 2007/0175958 A1, mentioned above, the instrument 10 may include an end-of-stroke sensor for sensing the end of the cutting stroke by the cutting instrument in the end effector and a beginning-of-stroke sensor for sensing the beginning of the cutting stroke by the cutting instrument. The signals from these sensors may be used to control the motor, for example.

Figure 4:
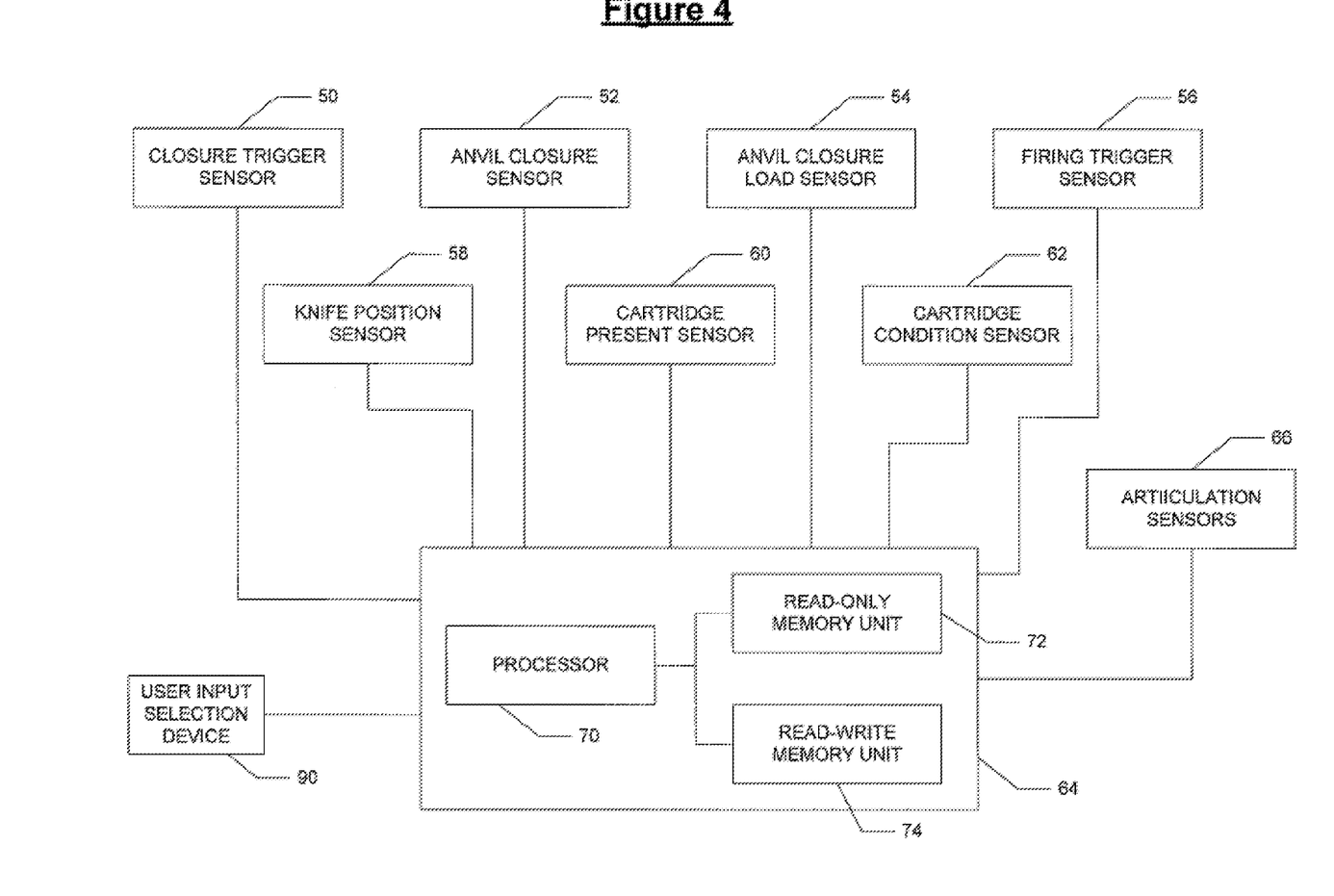
FIG. 4 is a block diagram depicting a control unit and sensors of the surgical according to various embodiments of the present invention.

In addition, with reference to FIG. 4, the instrument 10 may comprise: a closure trigger sensor 50 for sensing retraction of the closure trigger 18; an anvil closure sensor 52 for sensing closure of the anvil 24; an anvil closure load sensor 54 for sensing force exerted on the sensor 54, which may be placed on an inside bottom surface of the staple cartridge 22, by the staple cartridge 22 due to the closing of the anvil 24; a firing trigger sensor 56 for sensing retraction of the firing trigger 20; a knife position sensor 58 for sensing the longitudinal position of the knife (i.e., cutting instrument) along the channel 22 in the end effector 12; a cartridge present sensor 60 for sensing whether a staple cartridge 34 is present in the end effector 12; and a cartridge condition sensor 62 for sensing the condition of the staple cartridge 34 (e.g., whether the cartridge has been used or not).

The sensors 50-62 may be in communication with a control unit 64, preferably located in the handle 6 of the instrument. The control unit 64 may comprise a processor 70, a read-only memory unit 72, and a read-write memory unit 74. The control unit 64 may also comprise analog-to-digital converters (ADC) and digital-to-analog converters (DAC) (not shown) for communicating with the sensors 50-62. The read-only memory unit 72 may comprise EPROM and/or flash EEPROM memory units. The read-write memory unit 74 may comprise a volatile memory unit such a random access memory (RAM) unit. The various components of the control unit 64 may be discrete or they may be integrated in one or a few components. For example, in one embodiment, the processor 70, ROM 72, RAM 74, DACs, and ADCs may be part of a microcontroller or computer-on-a-chip.

The control unit 64 may be powered by a power source 76, such as a battery. For instruments 10 having a DC motor for powering the end effector, the power source 76 that powers the control unit 64 may be the same power source that powers the motor, or different power sources may be used for the control unit 64 and the motor.

Output from the various sensors may be stored in digital form in one or both of the memory units 72, 74. Published U.S. patent application Pub. No. 2007/0175964 A1, which is incorporated herein by reference in its entirety, discloses an endocutter having a memory device for storing and recording sensor data. The output from some of the above-mentioned sensors may be in analog form. For such types of sensors, the ADCs may be used to convert the analog sensor signals to digital form for storing in the memory units 72, 74. Also, the sensors may be coupled to the control unit 64 via wired and/or wireless communication links. For embodiments where the sensors communicate with the control unit 64 wirelessly, the sensors may comprise transponders that communicate with a transceiver (not shown) of the control unit 64.

Figure 5:
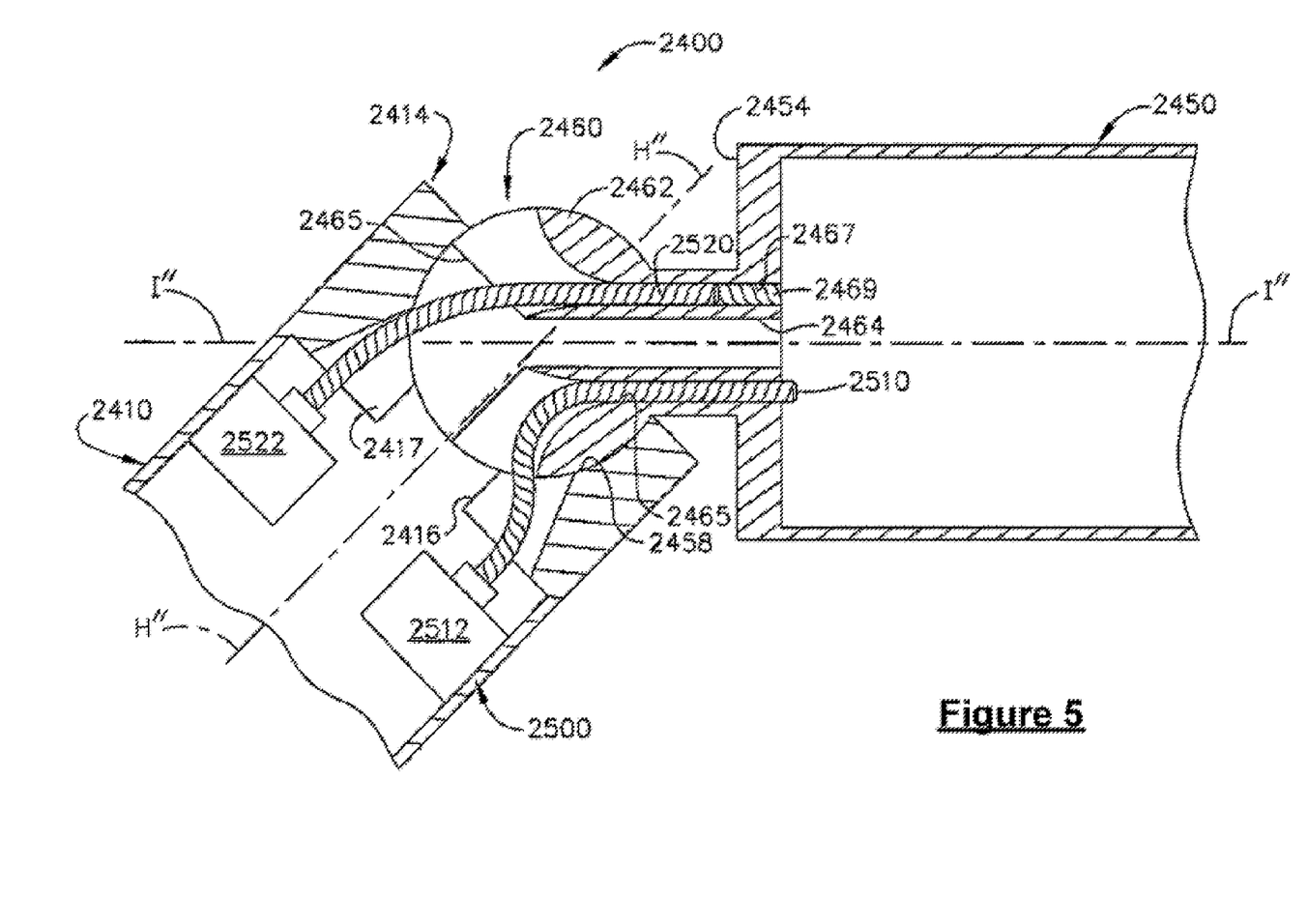
FIG. 5 is a diagram of a joint articulation assembly of the surgical instrument of according to various embodiments of the present invention.

According to various embodiments, the instrument 10 may comprise a motorized articulation pivot. FIG. 5 discloses an articulation pivot joint assembly 2400 according to such an embodiment. As can be seen in FIG. 5, distal tube segment 2410 has a proximal end 2414 and a distal axis H"-H". Although not shown in FIG. 5, the distal tube segment 2410 has a distal end that is mechanically coupled to the end effector 12. Depending upon the anvil closure arrangement employed, the distal end may be non-movably attached to the end effector body or by a cable, flexible member, or pivotable member. The distal tube 2410 segment may be partially hollow with the proximal end 2414 being solid with a hose/wire receiving passage 2416 therethrough. The passage 2416 may have a conical shaped portion 2417. The joint assembly 2400 further includes a proximal tube segment 2450, that has a distal end 2454, and a proximal axis I"-I". Although not shown in FIG. 5, the proximal tube segment 2450 has a proximal end that is attached to the handle assembly 6.

In one embodiment, the distal tube segment 2410 is pivotally coupled to the proximal tube segment 2450 by a ball joint assembly 2460. In one embodiment, the ball joint assembly 2460 comprises a ball member 2462 that is mounted to or is formed on the distal end 2454 of the proximal tube segment 2450. The ball member 2462 has a hollow passageway 2464 that has a flared or otherwise enlarged end portion 2465 to enable it to communicate with the passageway portions 2416, 2417 such that, regardless of the position of the ball member 2462, the hoses 480 and/or wires extending therethrough will not be pinched or otherwise damaged. The ball member 2462 is received in a socket 2458 provided in the proximal end 2414 of the distal tube segment 2410, such that the ball member 2462 is free to rotate therein.

In one embodiment, an actuation assembly, generally designated as 2500, is employed to articulate the distal tube segment 2410 relative to the proximal tube segment 2450. As can be seen in FIG. 5, in one non-limiting embodiment, two flexible worm gear cables 2510, 2520 are employed. The first flexible worm gear cable 2510 is adapted to drivingly engage worm gear teeth, threads, etc. (not shown) within a first gear passage 2465 formed in the ball member 2462. The first flexible worm gear cable 2510 is coupled to a first motor 2512 that is mounted within the distal tube segment 2410. Similarly, in this non-limiting embodiment, a second flexible worm gear cable 2520 is adapted to drivingly engage gear teeth, threads, etc. within a second gear passage 2467 formed in the ball member 2462 that has worm gear teeth, threads, etc. 2469 formed therein. The second flexible worm gear cable 2520 is coupled to a second motor 2522 mounted in the distal tube segment 2410. While described herein as "flexible worm gear cables," it will be understood that this term is meant to encompass all types of flexible driven cable or driver arrangements that do not necessarily employ worm gear-type teeth thereon.

The first and second motors 2512, 2522 may be electrically powered by a battery (e.g., a local battery or a battery pack in the handle 6) or by alternating current, or may be powered by hydraulic fluid or air. In one embodiment, the motors 2512, 2522 are electric powered and are operated by one or more switches or buttons on handle assembly 6. By controlling the amount of rotation and the direction of rotation of the first and second worm gear cables 2510, 2520, the ball member 2462 is caused to rotate within the socket 2458 and thereby articulate the distal tube segment 2410 (and the end effector 12 attached thereto) relative to the proximal tube segment 2450. The reader will appreciate that such arrangement facilitates left articulation as shown in FIG. 5 and right articulation (not shown). Again, however, the reader will appreciate that, while two flexible worm gear cable/motor arrangements have been described above, other embodiments of the present invention may employ only one flexible worm gear cable arrangement if only one-degree articulation is needed or desired. Also, while the ball member 2462 has been described as being non-movably mounted to the proximal tube segment 2450 with the socket 2458 provided in the distal tube segment 2410, those of ordinary skill in the art will understand that the ball member 2462 may be non-movably attached to the distal tube segment 2410 and the socket 2458 provided in the proximal tube segment 2450 in other non-limiting embodiments without departing from the sprit and scope of the present invention.

The joint assembly 2400 may include one or more sensors 66 (see FIG. 4) that sense the articulation of the articulation pivot 14. The output from the sensors 66 is recorded in one or both of the memory devices 72, 74 of the control unit 64. For example, the sensors 66 may include optical or magnetic rotary sensors (e.g., Hall effect sensors) and/or accelerometers that sense, collectively, the articulation, either directly or indirectly, of the end effector 12. For example, the sensors 66 may directly sense the articulation/rotation of the end effector. In another embodiment, the sensors 66 may sense the rotation and direction of the worm gear cables 2510, 2520 to sense thereby indirectly the articulation of the end effector 12. The control unit 64 may store and record the information from the articulation sensors 66, which may facilitate the user of the instrument 10 in replicating the exact or approximate articulation in a subsequent use of the instrument, as described further below. The sensors 66 may communicate with the control unit 64 via wired and/or wireless communication links. Also, the output from the sensors 66 may be analog signals that are converted to digital form by ADCs of the control unit 64.

Published U.S. patent application Pub. No. 2007/0106317 A1, entitled "Hydraulically and electrically actuated articulation joints for surgical instruments," by Shelton et al., describes in more detail a motorized articulation pivot. This application also provides other embodiments for motorized articulation pivots. This application also described hydraulically powered articulation pivots. For instruments having hydraulic articulation pivots, the articulation sensors 66 may include accelerometers or other suitable sensors for sensing, directly or indirectly, the articulation of the end effector 12.

The selection device 90 (see FIGS. 1-2) may be a multi-state or 1-state device according to various embodiments. For a multi-state device, the user of the instrument may activate the switch to cause it to articulate to a prior state of articulation (e.g., the immediately prior state of articulation) when the instrument 10 was last fired. The user may then activate the switch again to return the end effector 12 to its normal, unarticulated state. The user may also activate the device 90 to record the articulation data in the control unit 64 when the clinician has positioned the end effector in a desired state. In another embodiment, the articulate sensor data may be automatically recorded every time the instrument 10 is fired and/or clamped. That way, the clinician does not need to take an affirmative action, other than firing the instrument, such as pressing the device 90, to have the articulation data from the articulation sensors 66 recorded in the memory units 72, 74 of the control unit.

For an embodiment having multiple, 1-state input devices 90, 92, the user may use one input device 90 to articulate automatically the end effector to the prior state, and the second input device 92 to return the end effector 12 to its normal, unarticulated state. The input devices 90, 92 may be in communication with the control unit 64. There may also be a third input device (not shown) that the user may activate to cause the articulation data to be recorded in the control unit 64. Alternatively, the articulation sensor data may be automatically recorded every time the instrument 10 is fired and/or clamped.

To automatically articulate the end effector, when the selection device 90 is activated by the user, the control unit 64 may transmit signals to the motors 2512, 2522 in the joint assembly 2400 of the articulation pivot 14 (or hydraulic actuators for a joint assembly having hydraulic actuators). The signals sent to the motors 2512, 2522 may be based on the prior state of articulation of the end effector (e.g., the rotation and direction of the end effector 12 relative to the shaft) that is stored in one or both of the memory units 72, 74 based on the sensor data received from the articulation sensors 66. That way, by activating the selection device 90, the user of the instrument 10 may cause the end effector 12 to articulate automatically to the same articulation state in a prior use (e.g., the articulation state when the instrument 10 was last fired). This may be advantageous for procedures where the clinician has to make repeated cutting/fastening strokes in the same general location of the patient. Instead of having to articulate the end effector 12 each time to the same general location, the clinician could automatically articulate the end effector 12 to its last position by activating the selection device 90.

The following describes one example of how the instrument 10 may be used. In this example, a multi-state user input selection device 90 is assumed, recognizing that the example can be extended readily to an embodiment having two or more input devices. In this example, the clinician could insert the end effector 12 through the cannula. Then, using the manual articulation control 16, the clinician could articulate the end effector 12 to the desired position, that is, the position where the clinician desires to execute the simultaneous cutting and fastening actions of the cutting instrument 10. After the clinician has articulated the end effector 12 to the desired position, the clinician may retract the closure trigger to its locked position, locking tissue between the opposing jaws 22, 24 of the end effector 12. Then the clinician may retract the firing trigger 20, causing the cutting instrument 32 to (1) traverse longitudinally the channel 22 of the end effector 12, thereby cutting the tissue clamped in the end effector 12, and (2) cause the staples in the staple cartridge 34 to be urged up through the clamped tissue and turned by the anvil 24, thereby stapling the clamped tissue on each side of the incision created by the cutting instrument 32. Prior to or after firing, or prior to or after clamping, the user may activate the input device 90 (or some other input device) to cause the articulation data from the articulation sensors 66, indicating The state of the articulation of the end effector 12 relative to the shaft 8, to be recorded by the control unit 64. In another embodiment, the articulation data is recorded when the instrument is fired or when the end effector is clamped.

Then the clinician may automatically dearticulate the end effector 12 back to its normal, unarticulated state (e.g., straight) by pressing the user selection input device 90 (for a one-input, 2-state device embodiment, or the user selection input device 92 for a 2-input device embodiment) so that the clinician can withdraw it back through the cannula. Then the clinician can replace the spent staple cartridge 34 with a new one (i.e., one with staples) and insert the end effector 12 back through the cannula into the patient. Then, by pressing or otherwise activating the user input selection device 90, the clinician can cause the end effector 12 to articulate automatically to the same articulation position it was in when the instrument 10 was last fired based on the articulation sensor output from the last firing stored in the control unit 64. That way, the clinician can articulate automatically the end effector 12 back to the same general position it was in for the last firing, and not have to manual articulate the end effector 12. This should tend to lead to greater accuracy and repeatability in repositioning the end effector 12 when it is important to reposition it in the same general position as the prior firing.

Following the second firing of the instrument 10, the clinician may automatically dearticulate back to the unarticulated position, withdraw it through the cannula, and, if necessary, replace the staple cartridge again and reinsert the end effector for the next firing, with the end effector being automatically articulated to its state of articulation for the previous firing. For instruments that where the user activates a user input device to cause the articulate data to be recorded, the user could record the articulate state for just the first firing, so that for subsequent firings, the end effector 12 would be articulated automatically to the same general position as the first firing. Alternatively, user could record the articulation state for each firing, so that the end effector would be articulated automatically to the same general position as the immediately preceding firing The devices disclosed herein can be designed to be disposed of after a single procedure (which may comprise multiple firings), or they can be designed to be used in multiple procedures. In either case, however, the device can be reconditioned for reuse after at least one procedure. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the invention described herein will be processed before surgery. First, a new or used instrument is obtained and if necessary cleaned. The instrument can then be sterilized. In one sterilization technique, the instrument is placed in a closed and sealed container, such as a thermoformed plastic shell covered with a sheet of TYVEK. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam and other methods.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The various embodiments of the present invention represent vast improvements over prior staple methods that require the use of different sizes of staples in a single cartridge to achieve staples that have differing formed (final) heights.

Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., cannula or trocar). On the contrary, it is believed that the present invention may find use in any procedure where access is limited, including but not limited to laparoscopic procedures, as well as open procedures. Moreover, the unique and novel aspects of the various staple cartridge embodiments of the present invention may find utility when used in connection with other forms of stapling apparatuses without departing from the spirit and scope of the present invention.

What is claimed is:

1. A method of performing a medical procedure on a patient, the method comprising:
   (a) inserting an articulatable end effector of a surgical cutting and fastening instrument into the patient through a cannula, wherein the end effector is in a first articulation state when the end effector is inserted through the cannula;
   (b) after step (a), manually articulating the end effector to a second articulation state that is different from the first articulation state;
   (c) after step (b), firing the surgical cutting and fastening instrument to sever and fasten tissue clamped in the end effector;
   (d) after step (c), activating an input device on the surgical cutting and fastening instrument to cause the end effector to automatically articulate to the first articulation state;
   (e) after step (d), withdrawing the end effector from the patient through the cannula;
   (f) after step (e), replacing a staple cartridge on the end effector with a second staple cartridge;
   (g) after step (f), inserting the articulatable end effector of the surgical cutting and fastening instrument into the patient through the cannula, wherein the end effector is in a first articulation state when the end effector is inserted through the cannula;
   (h) after step (g), activating the input device on the surgical cutting and fastening instrument to cause the end effector to automatically articulate to the second articulation state;

(i) after step (h), firing the surgical cutting and fastening instrument to sever and fasten tissue clamped in the end effector;

(j) after step (i), activating the input device to cause the end effector to automatically articulate to the first articulation state; and (k) after step (j), withdrawing the end effector from the patient through the cannula.

2. The surgical instrument of claim 1, wherein controls the at least one motor to automatically articulate the automatically articulatable joint assembly to articulate from the second articulation state to the first articulation state when the automatic articulation input device is actuated and when the articulatable joint assembly is in the second articulation state.

3. A surgical instrument comprising:
   a handle;
   an end effector;
   a shaft connected to the handle;
   an automatically articulatable joint assembly connected between the end effector and the shaft for articulating the end effector relative to the shaft, wherein the automatically articulatable joint assembly comprises:
      at least one articulation sensor for sensing articulation of the automatically articulatable joint assembly, wherein the at least one articulation sensor is located adjacent to the end effector; and
      at least one motor for automatically articulating the end effector relative to the shaft, wherein the at least one motor is located between the end effector and the shaft;
   a manual articulation control adjacent to the handle that articulates upon user manipulation the end effector relative to the shaft from a first articulation state to a second articulation state;
   an automatic articulation input device on the handle; and
   a control unit in communication with the at least one articulation sensor and the automatic articulation input device, wherein the control unit comprises at least one memory unit for storing articulation data indicative of the second articulation state from the at least one articulation sensor, and wherein the control unit is in communication with the at least one motor of the automatically articulatable joint assembly and controls the at least one motor to automatically articulate the automatically articulatable joint assembly to articulate from the first articulation state to the second articulation state when the automatic articulation input device is actuated and when the articulatable joint assembly is not in the second articulation state.

4. The surgical instrument of claim 3, wherein the at least one motor comprises an electric motor.

5. The surgical instrument of claim 3, wherein the at least one motor comprises a hydraulic motor.

6. The surgical instrument of claim 3, wherein the control unit is in the handle.

7. The surgical instrument of claim 3, wherein the end effector comprises:
   a first jaw member; and
   a second jaw member pivotably connected to the first jaw member.

8. The surgical instrument of claim 7, wherein the control unit comprises a processor in communication with the at least one memory unit.

9. A surgical cutting and fastening instrument comprising:
   an end effector comprising:
      a moveable cutting instrument for cutting an object positioned in the end effector;
      a first jaw member comprising an elongate channel for carrying the cutting instrument; and
      a second jaw member pivotably connected to and opposing the first jaw member;
   a shaft;
   an automatically articulatable joint assembly joint assembly connected between the end effector and the shaft for articulating the end effector relative to the shaft, wherein the automatically articulatable joint assembly comprises:
      at least one articulation sensor for sensing articulation of the automatically articulatable joint assembly, wherein the at least one articulation sensor is located adjacent to the end effector; and
      at least one motor for automatically articulating the end effector relative to the shaft wherein the at least one motor is located between the end effector and the shaft;
   a manual articulation control that articulates upon user manipulation articulation the end effector relative to the shaft from a first articulation state to a second articulation state;
   a handle connected to the shaft, wherein the manual articulation control is adjacent to the handle, and wherein the handle comprises:
      an automatic articulation input device; and
      a control unit in communication with the at least one articulation sensor and the automatic articulation input device, wherein the control unit comprises at least one memory unit for storing articulation data indicative of the second articulation state from the at least one articulation sensor, and wherein the control unit is in communication with the at least one motor of the automatically articulatable joint assembly and controls the at least one motor to automatically articulate the automatically articulatable joint assembly to articulate from the first articulation state to the second articulation state when the automatic articulation input device is actuated and when the articulatable joint assembly is not in the second articulation state.

10. The surgical instrument of claim 2, wherein the first articulation state is zero-articulation state.

11. The surgical instrument of claim 9, wherein controls the at least one motor to automatically articulate the automatically articulatable joint assembly to articulate from the second articulation state to the first articulation state when the automatic articulation input device is actuated and when the articulatable joint assembly is in the second articulation state.

12. The method of claim 1, further comprising:
   (l) after step (k), replacing the second staple cartridge on the end effector with a third staple cartridge; and
   (m) repeating steps (g) through (k).

* * * * *